United States Patent [19]

Forquy et al.

[11] Patent Number: 5,075,505

[45] Date of Patent: Dec. 24, 1991

[54] PROCESS FOR OBTAINING N,N-DIMETHYL-N-ALKYLAMINES

[75] Inventors: Christian Forquy, Monein; René Brouard, L'Isle Adam, both of France

[73] Assignee: Ceca, S.A., Paris, France

[21] Appl. No.: 460,962

[22] PCT Filed: Jul. 5, 1989

[86] PCT No.: PCT/FR89/00352

§ 371 Date: Feb. 26, 1990

§ 102(e) Date: Feb. 26, 1990

[87] PCT Pub. No.: WO90/00539

PCT Pub. Date: Jan. 25, 1990

[30] Foreign Application Priority Data

Jul. 8, 1988 [FR] France .............................. 88 09280

[51] Int. Cl.$^5$ ............................................. C07C 209/50
[52] U.S. Cl. ..................................... 564/488; 564/480

[58] Field of Search ................. 564/480, 488; 568/885, 568/862; 502/318

[56] References Cited

U.S. PATENT DOCUMENTS

| | | | |
|---|---|---|---|
| 2,166,971 | 7/1939 | Schmidt et al. | 564/448 |
| 3,190,922 | 6/1965 | Le Bard et al. | 260/583 |
| 3,260,683 | 7/1966 | Endler | 568/885 |
| 3,444,204 | 5/1969 | Schütt | 260/583 |
| 4,310,697 | 1/1982 | Cheminal et al. | 564/480 |
| 4,495,369 | 1/1985 | Werner et al. | 564/480 |
| 4,533,648 | 8/1985 | Corrigan et al. | 568/885 |
| 4,855,515 | 8/1989 | Morris et al. | 568/862 |

Primary Examiner—Glennon H. Hollrah
Assistant Examiner—Peter G. O'Sullivan

[57] ABSTRACT

The process of making N,N-dimethyl-N-alkylamines containing less than 1% of alkanols by hydrogenation of N,N-dimethylalkylamines on a catalyst of the copper chromite type containing an amount of manganese oxide effective to keep the alkanol level below 1%.

7 Claims, 1 Drawing Sheet

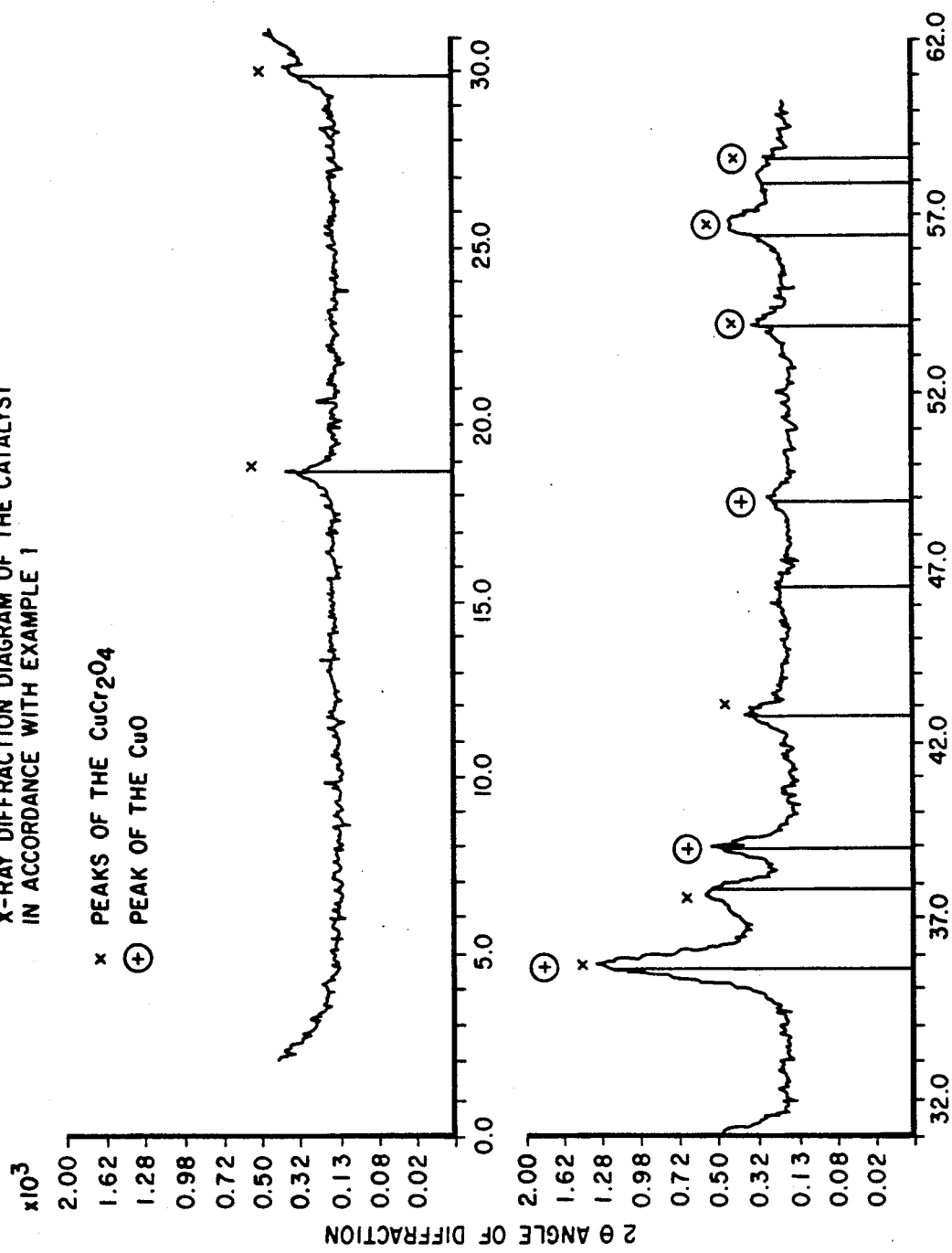

PROCESS FOR OBTAINING N,N-DIMETHYL-N-ALKYLAMINES

BACKGROUND OF THE INVENTION

1. Technical Field

The present invention pertains to an improved process for obtaining long-chain N,N-dimethyl-N-alkylamines by catalytic hydrogenation of the corresponding dimethylamides.

It involves obtaining by this route N,N-dimethylamines free of heavy alcohols and intended, among other applications, for the manufacture of quaternary ammonium salts for industrial detergents, bactericides or disinfectants.

2. Prior Technique

The procedure is known for producing N,N-dimethyl-N-alkylamines by reaction of the dimethylamine with an alkyl halogen, a fatty alcohol or an alpha-olefin. These are industrial routes, but they involve expensive raw materials.

A more economic route involves reacting the dimethylamine on a fatty acid to form the N,N-dimethylaklylamide, then hydrogenating the fatty N,N-dimethylalkylamide to the N,N-dimethyl-N-alkylamine. Many modes of industrial realization are known, which operate by catalytic hydrogenation under hydrogen pressure; for example:

(i) the procedure presented in U.S. Pat. No. 3,190,922 filed by General Mills operates on a copper chromite catalyst which, it is said incidentally, can be stabilized with barium oxide, in the presence of dimethylamine and under a circulating hydrogen stream. However, the catalysts used, whether or not they are stabilized with barium, turn out to lose too large a portion of their activity and their selectivity;

(ii) the procedure according to U.S. Pat. No. 3,444,204, which is a continuous procedure based on the use of catalysts of the same type, in a fixed bed under high pressure (250 bars);

(iii) the procedure described by L. Pashkova and M. Yakushkin in *J. of Applied Chem. of USSR*, 53, 8, pp. 1398–1401 (1980), which is distinguished from the preceding essentially in that one operates at atmospheric pressure; and (iv) U.S. Pat. No. 4,448,998 of Procter and Gamble, which represents an attempt to improve the quality of the finished raw products, with use of a hydrogenation catalyst of copper chromite combined with a proportionate amount of non-catalytic zeolite (18% in relation to the charge), so as to capture the water produced during the hydrogenation of the amide and to minimize the parasitic reactions that it generates.

These known procedures of the prior art have in common the drawbacks of not providing fatty N,N-dimethyl-N-alkylamine of the desired quality for at least two reasons.

First, the purity of the final product is insufficient and, specifically, the content of fatty alcohols is too high. These alcohols are very difficult to separate out by distillation since they boil very close to the N,N-dimethyl-N-alkylamines and it involves not just separating a fatty alcohol from the homologous N,N-dimethyl-N-alkylamine, but separating a group of fatty alcohols from a group of N,N-dimethyl-N-alkylamines, the distribution of the chains of which is that of the fatty acids from the source oils, i.e., coconut oil, palm oil, etc. It is easy to comprehend this from the table below of the comparative boiling temperatures under 20 mm of mercury (2.7 kPa) for the N-N-dimethyl-N-alkylamines and the n-alkanols:

| Length of alkyl chain | 8C | 10C | 12C | 14C | 16C | 18C |
|---|---|---|---|---|---|---|
| N,N-dimethylalkylamine | 71 | 112 | 140 | 169 | 191 | 215 |
| Alkanol | 101 | 126 | 150 | 177 | 198 | 220 |

Second, the economically necessary recycling of the copper chromite catalyst leads to a decrease in its activity and accentuates its non-specificity, which is balanced in each cycle by an increase in the content of alcohols.

SUMMARY OF THE INVENTION

It has now been found that the use of a catalyst made of copper chromite doped with manganese makes it possible in a completely unexpected manner to resolve the reported problems.

The present invention is comprised of a process for obtaining N,N-dimethyl-N-alkylamines of general formula

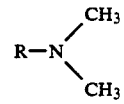

in which R is an alkyl or alkenyl radical with 12 to 24 carbon atoms and, preferentially, amines with C12–C14 alkyl chains, containing less than 1% fatty alcohols, by catalytic hydrogenation of the corresponding N,N-dimethylalkylamides, using copper chromite type catalysts under a circulating hydrogen stream, at pressures between 10 and 100 bars, and at temperatures between 220° and 280° C., with the catalyst containing manganese oxide in addition to copper oxide and copper chromite.

DETAILED DESCRIPTION

"Doped copper chromite catalyst" is understood to means compositions essentially based on copper and chromium oxides, containing several percent of an oxide of another metal, such as barium, magnesium or calcium, the role of which is to stabilize the catalyst by delaying the reduction in the copper when the catalyst operates in hydrogenation, leading to a certain loss of activity and of selectivity. Copper chromite catalysts doped with barium are used for catalyzing the hydrogenation of aldehydes into alcohols. It was not known that copper chromites doped with manganese were advantageous for the hydrogenation of amides into amines which are practically free of alcohols. It is the unexpected behavior of such a catalyst which is exploited in the invention for producing N,N-dimethyl-N-alkylamines of the desired quality.

To prepare the catalyst for use in the invention, one can operate:

(i) either by coprecipitation with a base of the copper, chromium and manganese oxides from a solution of their salts; or (ii) by coprecipitation with a base of the copper and manganese oxides on chromic oxide; or (iii) by thermal decomposition of a mixed salt of copper and chromium in the presence of manganese oxide or a manganese salt.

The product of the thermal decomposition or coprecipitation is washed and dried in an oven, then calcined under air at a temperature higher than 350° C., but not exceeding 600° C., and preferably a temperature on the order of 450° C., then reduced, preferably with hydrogen, at a temperature between 100° and 300° C.

The catalyst compositions according to the invention contain from 10 to 75% by weight of copper oxide (CuO), from 10 to 75% of chromium oxide ($Cr_2O_3$ and of manganese oxide ($MnO_2$)in an amount effective to keep the alkanol level below 1%; i.e., about 2 to 20% of $MnO_2$. Preferred compositions contain from 45 to 49% of CuO, 46 to 49% of $Cr_2O_3$ and 2 to 10% of $MnO_2$. The catalyst most frequently is in the form of a black powder, but it can be in the form of tablets or extruded granules. In addition, some of these compositions are available commercially.

With regard to the general operation of the discontinuous procedure for manufacturing N,N-dimethyl-N-alkylamines according to the invention, the following description constitutes the best mode of realization of the invention.

One employs reactors equipped with a turbine and agitation blades, constructed so as to be able to operate at a pressure on the order of 100 bars, which is charged with the N,N-dimethylalkylamide and from 0.5 to 20% by weight of catalyst; the amounts of around 5% are those which will be employed in practice.

It is necessary to evacuate the water formed by the reaction:

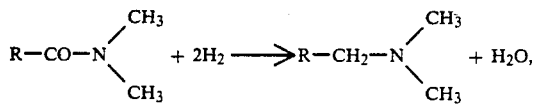

in order to permit its advancement and to avoid blockage of the catalyst. Circulating hydrogen under pressure is used for this. The water is condensed and the hydrogen is recycled by means of a blower.

The reaction is made to evolve at temperatures between 180° and 300° C., and preferentially between 220° and 280° C., and under a total pressure between 10 and 100 bars. The reaction proceeds more rapidly under elevated pressure, but to the detriment of the selectivity, notably due to a greater contribution to the production of alcohols according to the reaction:

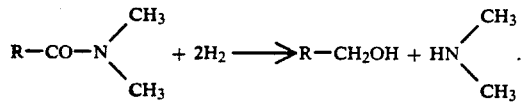

For this reason, it is preferable to operate between 10 and 50 bars.

The circulating hydrogen stream is between 0.2 liter of $H_2$/g of amide/hour and 2 liters of $H_2$/g of amide/hour (i.e., essentially between 0.2 mole $H_2$/mole amide/hour and 2 moles $H_2$/mole amide/hour). Selection of notably higher flow rates does not result in any improvement of the activity of the selectivity of the catalyst.

Although use of the catalyst doped with manganese and the specified operating conditions leads to a low level of alcohols in the reaction products, it is still necessary to transform into amines the alcohols which, nevertheless, have formed. This is realized by addition of dimethylamine, because of the following reaction:

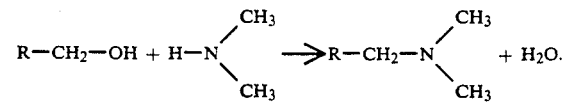

The proportion of dimethylamine generally does not exceed one molar percent (22.5% by weight) of the circulating hydrogen. It is advantageous not to introduce the dimethylamine until near the end of the reaction, when the alkalinity has reached around 75% of the theoretical alkalinity.

Taking into account the diffusional limitations of the chemical compounds engaged in the reaction and, notably, the relatively low diffusion of the hydrogen into the amide in the absence of solvent, it is necessary to maintain vigorous agitation in the medium. Although the global kinetics are very sensitive to the agitation rate, beyond a certain limit one does not observe any noteworthy increase in the reaction rate. This limit is obviously a function of the apparatus employed. It is this experimental limit which appears in the examples given below as illustrations.

The invention extends without difficulty to obtaining saturated N,N-dimethyl-N-alkylamines other than the alkyl-(C12–C14)-amines, notably to the N,N-dimethyl-N-alkylamines which originate from fatty acids of animal or plant origin, for example, the fatty acids of tallow (on average, C16–C18), soybean (on average, unsaturated C16–C18) or rape (on average, C18–C22), and can be transferred for obtaining homologues such as the N,N-diethyl-N-alkylamines from N,N-diethylalkylamides. Its adaptation to a continuous procedure for production of N,N-dimethyl-N-alkylamines is also within the ability of the expert in this field.

The invention will be further described in connection with the following examples which are set forth for purposes of illustration only.

EXAMPLE 1

Preparation of a Cu-Cr-Mn Catalyst

One prepares a Cu-Cr-Mn catalyst mass by mixing in 500 mL of distilled water, 89 grams of $Cu(NO_3)_2 \cdot 6H_2O$, 240 grams of $Cr(NO_3)_3 \cdot 9H_2O$ and 10 grams of Mn $(NO_3) \cdot 4H_2O$. The hydroxides are precipitated under agitation with addition of a 2M solution of $Na_2CO_3$ grams per liter of water) to a pH value of 6.5. The precipitate is filtered, washed abundantly with distilled water and the paste obtained in dried at 150° C. in an oven for 16 hours. After drying, the solid is ground into a fine powder (2 to 10 μm) and again calcined under air in an oven at a temperature of 450° C. The powder, which was initially green, turns black.

Thus, one obtains a catalyst with a true composition established at CuO=46%, $Cr_2O_3$ =46%, $MnO_2$ =4% with the percentages expressed as weight percent. This product is very partially crystallized. FIG. 1 shows the x-ray diffraction diagram, in which one can distinguish the characteristic peaks of chromite ($CuCr_2O_4$) and those of copper oxide (CuO). The manganese oxide peaks are absent, which testifies to the presence of manganese oxide in the amorphous phase.

EXAMPLE 2

One employs the catalyst of Example 1 in the hydrogenation of N,N-dimethylated amides of carbon-chain length essentially C12–C14 (0.15% of C8, 0.2% of C10, 66% of C12, 33% of C14).

Such N,N-dimethylakylamides are obtained industrially by direct amidation of the corresponding fatty acids with dimethylamine, for example by maintaining the fatty acid at 170°–190° C. for 10 to 16 hours under circulation of dimethylamine at 0.2–2 bars, then eliminating under vacuum the excess of dimethylamine trapped in the N,N-dimethylalkylamide formed. In the case of the present example, the dimethylamide employed has an amide alkalinity equal to 4.2 moles/kg and contains 0.44% of residual C12–C14 fatty acid and 0.02% of water.

One charges 400 g of this N,N-dimethyl-(C12–C14)-amide and 20 g of the Cu-Cr-Mn catalyst into a one-liter autoclave. After purging the reactor with nitrogen, under agitation with the blades at 2,000 r.p.m., the pressure is raised to 27 bars of pure hydrogen and a circulation is established of 400 L/hour of hydrogen. The temperature is raised to 235° C. at the rate of 5° C./minute and the hydrogen is then replaced by an H$_2$-dimethylamine mixture at 0.8% dimethylamine in 400 L/hour of H$_2$. Samples are collected to permit monitoring of the reaction kinetics either by measurement of the amide alkalinity or by chromatographic analysis. The reaction is stopped by temperature and agitation supply, and bringing the pressure to atmospheric pressure, fifteen minutes after obtaining a zero amide alkalinity.

The catalyst then decants in the hot state in the N,N-dimethyl-(C12–CC14)-amine formed, and the latter is collected by aspiration after decompression of the autoclave via an orifice located on the reactor cap. The catalytic paste remains at the bottom of the reactor.

For the following operations, the reactor is recharged with 400 grams of amide and 4 grams of Cu-Cr-Mn catalyst (primarily to compensate for the losses due to the collection of samples). The results obtained in the first operation on a new catalyst and in the five subsequent recycling operations are show in Table I.

It can be seen, on the one hand, that the total reaction time barely changes from one recycling to the next, which testifies to the catalytic stability, and the alcohol content of the finished products is maintained below 0.5%. The principal by-product of the reaction is the dialkylmethylamine, which can be easily separated from the alkyldimethylamine by distillation. Thus, one obtains fatty-chain ester in a proportion below 1%. The mean yield of alkyldimethylamine is 87.3% by weight.

TABLE I

Hydrogenation of C12–C14 dimethylalkylamide

Operating conditions
Cu/Cr/Mn catalyst: 20 g
Charge: 400 g
Gas flow rate of the H$_2$-DMA mixture at 0.8%: 400 l/h
Pressure: 27 bars
Temperature: 235° C.
Agitation 2000 rpm Composition Weight %

| Recycle number | Reaction Time | Amide conversion | Amine alkalinity (mole/kg) | R—OH | R—N(CH$_3$)(CH$_3$) | R\N—CH$_3$ / R | R$^{-1}$—C(=O)—N(CH$_3$)(CH$_3$) | Heavy esters |
|---|---|---|---|---|---|---|---|---|
| New catalyst | 7 h 00 | 99.9% | 4.2 | 0.3 | 88.5 | 10.5 | 0.1 | 0.6 |
| 1st | 7 h 45 | 99.8% | 4.2 | 0.5 | 88.7 | 12.5 | 0.2 | 0.1 |
| 2nd | 9 h 00 | 100.0% | 4.2 | 0.0 | 88 | 11.9 | 0.0 | 0.1 |
| 3rd | 9 h 00 | 99.4% | 4.2 | 0.4 | 87.7 | 10.4 | 0.6 | 0.9 |
| 4th | 9 h 00 | 99.8% | 4.2 | 0.3 | 89.3 | 9.8 | 0.2 | 0.4 |
| 5th | 9 h 30 | 99.7% | 4.2 | 0.2 | 84.1 | 14.8 | 0.3 | 0.6 |

In the present table, R has the following meaning: C12–C14 hydrocarbon chain with 0.15% of C8, 0.2% of C10, 66% of C12, 33% of C14.
R$^{-1}$C(=O)— represents chains with the same distribution of carbons.

EXAMPLE 3

For purposes of comparison, we applied the same operating conditions as in Example 2, notably by carrying out the same type of recycling, but with a Cu-Cr-Ba catalyst containing 40% of CuO, 45.5% of Cr$_2$O$_3$ and 9.5% of BaO, the specific surface of which was 36 m$^2$/g. This catalyst was prepared as in Example 2, with the difference of using Ba(NO$_3$)$_2$·H$_2$O in place of Mn(NO$_3$)·4H$_2$O.

The results obtained in the first operation with a new catalyst and in the three subsequent operations on a recycled catalyst are shown in Table II.

We can see here the increase in the reaction time required for the conversion of the N,N-dimethylated amide due to the deactivation of the catalyst. In addition, we see that the alcohol level cannot be brought to a level below 3%, which is a latent defect. Continuation of the reaction beyond the time required for total conversion does not succeed in reducing these alcohol levels.

TABLE II

Hydrogenation of C12–C14 dimethylaklylamide

Operating conditions
Cu—Cr—Ba catalyst: 20 g
Charge: 400 g
Gas flow rate of the H$_2$DMA at 0.8%: 400 l/h
Pressure: 27 bars
Temperature: 235° C.
Agitation: 2000 rpm Composition Weight %

TABLE II-continued

| | | | | | | | | | |
|---|---|---|---|---|---|---|---|---|---|
| Recycle number | Reaction Time | Amide conversion | Amine alkalinity (mole/kg) | R—OH | R—N(CH$_3$)(CH$_3$) | R₂N—CH$_3$ | R⁻¹—C(=O)—N(CH$_3$)(CH$_3$) | | Other heavy Components |
| New catalyst | 7 h 00 | 99.5% | 4.2 | 3.5 | 88.3 | 7 | 0.6 | | 0.6 |
| 1st | 7 h 45 | 99.3% | 4.1 | 7.1 | 85.5 | 5.7 | 0.7 | | 1.0 |
| 2nd | 9 h 00 | 97.2% | 4.2 | 5.0 | 84.8 | 7 | 2.8 | | 0.4 |
| 3rd | 11 h 00 | 99.5% | 4.0 | 4.1 | 86.1 | 8.5 | 0.5 | | 0.8 |
| 4th | 10 h 45 | 96.7% | 3.8 | 8.6 | 80.7 | 6.4 | 3.3 | | 1.0 |

See Table I for the meaning of R and R⁻¹—C(=O)—.

EXAMPLE 4

In this comparative example, we used a non-doped copper chromite catalyst, resulting from preparation in accordance with Example 1 without Mn(NO$_3$)$_3$·4H$_2$O.

The results of the catalytic tests during two recyclings are shown in Table III.

We can see that the catalyst is very active in its first use, but that the alcohol content of the finished products is very high (>10%) and that the reaction time increases very sharply during the subsequent recyclings without the ability to control the alcohol content.

TABLE III

Hydrogenation of C12–C14 dimethylalkylamide

Cu—Cr catalyst: 20 g
Charge: 400 g of amide
Gas flow rate of H$_2$— DMA at 0.8%: 400 l/h
Pressure: variable
Temperature: variable
Agitation: 2000 rpm
Composition Weight %

| Recycle number | Reaction Time | Amide conversion | Press. (bars) | Temp. (°C.) | Amine alkalinity mole/kg | R—OH | R—N(CH$_3$)(CH$_3$) | R$_2$N—CH$_3$ | R⁻¹—C(=O)—N(CH$_3$)(CH$_3$) | Other heavy Components |
|---|---|---|---|---|---|---|---|---|---|---|
| New catalyst | 6 h 00 | 100.0% | 50 | 235 | 3.8 | 10.9 | 80.7 | 7.2 | 0.2 | 1.0 |
| 1st | 9 h 15 | 99.6% | 27 | 240 | 4.1 | 4.9 | 86.7 | 7.0 | 0.5 | 0.9 |
| 2nd | 10 h 00 | 98.7% | 27 | 240 | 3.9 | 6.7 | 87.5 | 3.9 | 1.0 | 0.9 |

See Table I for the meaning of R and R⁻¹—C(=O)—.

EXAMPLE 5

Into a semi-industrial reactor, there is charged 100 kg of N,N-dimethylalkylamide obtained from an industrial C12–C14 fatty acid with a fatty chain distribution:
C12 acids 70%
C14 acids 30%,
and 5 kg of catalyst according to the invention, with a composition of 47% CuO, 49% Cr$_2$O$_3$ and 4% MnO$_2$. After purging the reactor with nitrogen, pure hydrogen was admitted to raise the total pressure to 30 bars, and a circulation of 100 m$^3$ P.T.N./hour of hydrogen was established. The temperature was raised progressively to 235° C. and these conditions were maintained for five hours. When the collected samples showed an alkalinity equal to or greater than 3.3 milliequivalents/gram, dimethylamine was introduced into the circulating stream at the rate of 1 mole % mole of hydrogen and the reaction was continued for another two hours. After termination of the circulation and decompression, the reactor was evacuated, the catalyst was allowed to decant and the supernatant was collected.

We thereby obtained a raw amine containing 93% dimethyl-(C12–C14)-amine.

The subsequent operations followed the same procedure after recharging 100 kg of N,N-dimethylalkylamide mixed with the catalytic paste recovered from the preceding operation and 0.5 kg of new catalyst. The tenth operation yielded 87 kg of raw amine with the following composition:
N,N-dimethyl-(C12–C14)-amine 92%
N-methyl-N,N-di-(C12–C14)-amine 7%
alcohol (C12–C14) 0.2%
other 0.8%

It should be noted that the 92% yield of raw amine is only an apparent yield. In fact, a non-negligible portion of fatty products (essentially amines with a small amount of amides) is entrained by the hydrogen stream, circulating at the same time as the water eliminated in the reaction. In an industrial operation, these products, referred to as fatty entrainments, are separated out and recycled into the following operation. In the present example, the recyclable fatty acid entrainments comprise 5 kg.

EXAMPLE 6

We proceeded as in Example 5, the difference being that use was made of a copra fatty acid with the following composition:
C8 acids 5.5%
C10 acids 6.3%
C12 acids 50.9%
C14 acids 18.3%
C16 acids 8.6%
C18 acids 9.7%

The tenth operation yielded 84 kg of raw amines and 8 kg of recyclable fatty entrainments.

EXAMPLE 7

We proceeded as in Example 5, with the difference that the dimethylamine was introduced as soon as the operating temperature (245° C.) was reached, at a moment when the developed alkalinity was still very weak. The raw amine obtained in the first cycle did not contain more than 90% tertiary amines of the dimethyl-(C12-C14)-amine type, which demonstrates the value of the practice in accordance with the invention of not introducing the dimethylamine until the alkalinity has been established at approximately 75% of the theoretical value.

While the invention has been described in connection with a preferred embodiment, it is not intended to limit the scope of the invention to the particular form set forth, but on the contrary, is intended to cover such alternatives, modifications, and equivalents as may be included with the spirit and scope of the invention as defined by the appended claims.

What is claimed is:

1. A process for obtaining N,N-dimethyl-N-alkylamines of general formula:

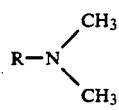

in which R is an alkyl or alkenyl radical with 12 to 24 carbon atoms, the said N,N-dimethyl-N-alkylamines containing less than 1% of alkanols, comprising hydrogenating N,N-dimethylalkylamides, under a circulating hydrogen stream, which has a molar ratio to the N,N-dimethylalkylamide between about 2 and 20, the total pressure being between about 10 and 100 bars, and the temperature being between about 220° and 280° C., on a catalyst of the copper chromite type containing manganese oxide in an amount effective to keep the alkanol level below 1%.

2. The process of claim 1, wherein the alkyl or alkenyl radical is comprised primarily of chains containing 12 to 14 carbon atoms, and that the N,N-dimethylalkylamide employed is a N,N-dimethylamide of copra acids.

3. The process of claim 1 or 2, wherein the weight distribution of the components, in percent by weight, in the catalyst is:
CuO 10–75%
$Cr_2O_3$ 10–75%
$MnO_2$ 2–20%

4. The process of claim 1 or 2, wherein the weight distribution of the components, in percent by weight, in the catalyst is:
CuO 45–49%
$Cr_2O_3$ 45–49%
$MnO_2$ 2–10%

5. The process of claim 1 or 2, wherein the catalyst is employed in a weight proportion in relation to the N,N-dimethylalkylamide between about 2 and 10% and the weight distribution of the components, in percent by weight, in the catalyst is:
CuO 45–49%
$Cr_2O_3$ 45–49%
$MnO_2$ 2–10%

6. The process of claim 1 or 2, wherein the catalyst is employed in a weight proportion in relation to the N,N-dimethylalkylamide between about 2 and 10%, the circulating hydrogen stream contains approximately 1% by volume of dimethylamine, and the weight distribution of the components, in percent by weight, in the catalyst is:
CuO 45–49%
$Cr_2O_3$ 45–49%
$MnO_2$ 2–10%

7. The process of claim 1 or 2 wherein the catalyst is employed in a weight proportion in relation of the N,N-dimethylamide between about 2 and 10%, the circulating hydrogen stream contains approximately 1% by volume of dimethylamine, and the weight distribution of the components, in percent by weight, in the catalyst is:
CuO 45–49%
$Cr_2O_3$ 45–49%
$MnO_2$ 2–10%
said dimethylamine being introduced into the circulating stream when the alkalinity has reached 75% of the expected theoretical value.

* * * * *